United States Patent [19]

Maurer et al.

[11] 4,094,975
[45] June 13, 1978

[54] O-ALKYL-O-CHLOROMETHYLSULFONYL-PHENYL-THIONOPHOSPHONIC ACID ESTERS AND NEMATICIDAL AND ARTHROPODICIDAL USE

[75] Inventors: Fritz Maurer; Hans-Jochem Riebel; Rolf Schröder, all of Wuppertal; Wilhelm Sirrenberg, Sprockhoevel; Ingeborg Hammann, Cologne; Bernhard Homeyer, Leverkusen; Herbert Thomas, Wuppertal, all of Germany

[73] Assignee: Bayer Aktiengesellschaft, Leverkusen, Germany

[21] Appl. No.: 764,798

[22] Filed: Feb. 2, 1977

[30] Foreign Application Priority Data

Feb. 13, 1976 Germany ............................ 2605889

[51] Int. Cl.² ........................... A01N 9/36; C07F 9/18
[52] U.S. Cl. ..................................... 424/216; 260/949
[58] Field of Search ......................... 260/949; 424/216

[56] References Cited

U.S. PATENT DOCUMENTS 2,803,580  8/1957  Metivier ............................... 424/216

FOREIGN PATENT DOCUMENTS 1,078,124  3/1960  Germany .............................. 260/949
1,183,494  12/1964  Germany .............................. 260/949

Primary Examiner—Richard L. Raymond
Attorney, Agent, or Firm—Burgess, Dinklage & Sprung

[57] ABSTRACT

O-Alkyl-O-chloromethylsulfonylphenyl-thionophosphonic acid esters of the formula

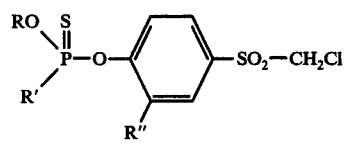

(I)

in which
R represents alkyl with 1 to 6 carbon atoms,
R' represents alkyl with 1 to 6 carbon atoms or phenyl and
R" represents hydrogen or halogen, which possess insecticidal, acaricidal and nematicidal properties.

10 Claims, No Drawings

O-ALKYL-O-CHLOROMETHYLSULFONYLPHE-NYL-THIONOPHOSPHONIC ACID ESTERS AND NEMATICIDAL AND ARTHROPODICIDAL USE

The present invention relates to and has for its objects the provision of particular new O-alkyl-O-chloromethylsulfonylphenyl-thionophosphonic acid esters which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from German Published Specification DAS No. 1,098,209, U.S. patent application Ser. No. 648,849, filed Jan. 13, 1976, now U.S. Pat. No. 4,013,794, and Australian patent specification No. 255,279 that O-phenylthiono(thiol)-phosphoric acid esters, for example O-ethyl-S-n-propyl-O-(4-chloromethylsulfonyl-(Compound A) and 2-chloro-4-chloromethylsulfonylphenyl)-(Compound B) or O-ethyl-S-methyl-O-(4-methylsulfonylphenyl)-thionothiolphosphoric acid ester (Compound C) and O,O-diethyl-O-(4-chloromethylsulfonylphenyl)-thionophosphoric acid ester (Compound D), possess insecticidal and acaricidal properties.

The present invention now provides, as new compounds, the O-phenylthionophosphonic acid esters of the general formula

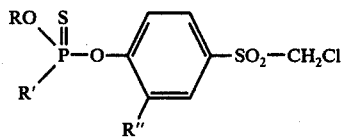

in which
R represents alkyl with 1 to 6 carbon atoms,
R' represents alkyl with 1 to 6 carbon atoms or phenyl and
R" represents hydrogen or halogen.

Preferably, R represents straight-chain or branched alkyl with 1 to 4 carbon atoms, R' represents straight-chain or branched alkyl with 1 to 3 carbon atoms or phenyl, and R" represents hydrogen, chlorine or bromine.

Surprisingly, the O-phenylthionophosphonic acid esters (I) according to the invention combine a very low toxicity to warm-blooded animals with a substantially greater insecticidal, acaricidal and nematicidal action than the previously known compounds of analogous structure and of the same type of action. The compounds according to the invention thus represent a genuine enrichment of the art.

The present invention also provides a process for the preparation of an O-phenylthionophosphonic acid ester of the formula (I), in which a substituted phenol of the general formula

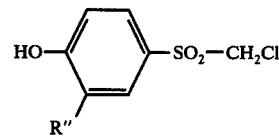

in which
R" has the above-mentioned meaning,
is reacted, as such in the presence of an acid acceptor or in the form of an alkali metal salt, alkaline earth metal salt or ammonium salt thereof, with an O-alkylthionophosphonic acid ester halide of the general formula

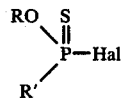

in which
R and R' have the above-mentioned meanings and
Hal represents halogen, preferably chlorine.

If, for example, O-isopropylthionomethanephosphonic acid ester chloride and 2-chloro-4-chloromethylsulfonylphenol are used as starting materials, the course of the reaction can be represented by the following equation:

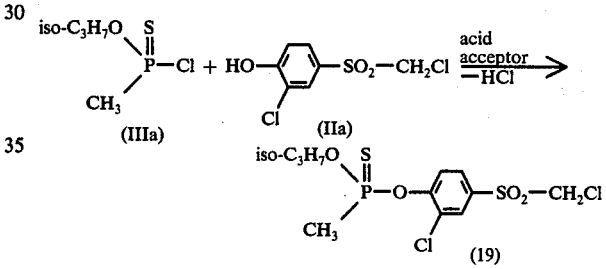

Substituted phenols (II) which can be used as starting materials are known from the literature; they are all preparable in accordance with customary processes as shown for example in U.S. patent application Ser. No. 648,849.

The following may be mentioned as individual examples: 2-chloro- and 2-bromo-4-chloromethylsulfonylphenol and 4-chloromethylsulfonylphenol.

The O-alkylthionophosphonic acid ester halides (III) also to be used as starting materials are known.

The following may be mentioned as examples of these compounds: O-methyl-, O-ethyl-, O-n-propyl, O-isopropyl-, O-n-butyl-, O-iso-butyl-, O-sec.-butyl- and O-tert.-butylmethane-, -ethane-, -n-propane-, -isopropane- and -benzene thionophosphonic acid ester chloride.

The process for the preparation of the compounds according to the invention is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

Instead of working in the presence of acid acceptors, it is equally possible first to prepare salts, preferably the alkali metal salts or ammonium salts, of the phenol derivatives (II), in the undiluted form, and subsequently to react these further.

The reaction temperature can be varied within a fairly wide range. In general, the reaction is carried out at between 0° and 120° C, preferably at 30° to 60° C.

In general, the reaction is allowed to take place under normal pressure.

To carry out the process, the starting materials are preferably employed in the equimolar ratio. An excess of one or other component produces no essential advantages. The reactants are in general mixed in one of the stated solvents and in most cases are stirred for from one to several hours at an elevated temperature in order to complete the reaction. An organic solvent, for example toluene, is then added to the mixture and the organic phase is worked up in the usual manner by washing, drying and distilling off the solvent.

The new compounds are obtained in the form of oils which in some cases cannot be distilled without decomposition, but are freed from the last volatile constituents by so-called "slight distillation", that is to say by prolonged heating under reduced pressure to moderately elevated temperatures, and are purified in this way. They are characterized by the refractive index. If the compounds are obtained in the solid form, they are crystalline and possess a sharp melting point.

As already mentioned, the O-phenylthionophosphonic acid esters according to the invention are distinguished by an outstanding insecticidal, acaricidal and nematicidal activity. They are not only active against plant pests, pests harmful to health and pests of stored products, but also, in the veterinary medicine field, against animal parasites such as nematodes, and they possess a low phytotoxicity and a good action against sucking and biting insects and against mites.

For this reason, the compounds according to the invention can be employed successfully as pesticides in plant protection as well as in the hygiene field, the field of protection of stored products and the veterinary field.

The active compounds are well tolerated by plants, have a favorable level of toxicity to warm-blooded animals, and can be used for combating arthropod pests, especially insects and arachnidae, and nematode pests which are encountered in agriculture, in forestry, in the protection of stored products and of materials, and in the hygiene field. They are active against normally sensitive and resistant species and against all or some stages of development. The above-mentioned pests include:

From the class of Isopoda, for example *Oniscus asellus, Armadillidium vulgare* and *Porcellio scaber,* from the class of the Diplopoda, for example *Blaniulus guttulatus;* from the class of the Chilopoda, for example *Geophilus carpophagus* and Scutigera spec.; from the class of the Symphyla, for example *Scutigerella immaculata,* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuhniella, Galleria mellonella, Cacoecia podana, Capua recticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleriae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp., from the order of the Diptera, for example Aedes pp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp, Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example, *Scorpio maurus* and *Latrodectus mactans;* from the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sacroptes spp., Tarsonemus spp., *Bryobia praetiosa,* Panonychus spp., and Tetranychus spp..

The plant parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides, acaricides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE A

Drosophila test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all the flies were killed; 0% meant that no flies were killed.

The active compounds, the concentrations of the active compounds, the evaluation times and the results can be seen from the following table:

Table 1

| (Drosophila test) | | |
|---|---|---|
| Active compound | Active compound concentration in % | Degree of destruction in % after 1 day |
| n-C₃H₇S-P(=S)(OC₂H₅)-O-C₆H₄-SO₂-CH₂-Cl (A) | 0.1<br>0.01 | 100<br>0 |

Table 1-continued

| (Drosophila test) | | |
|---|---|---|
| Active compound | Active compound concentration in % | Degree of destruction in % after 1 day |
| n-C₃H₇S-P(=S)(OC₂H₅)-O-C₆H₃(Cl)-SO₂-CH₂-Cl (B) | 0.1<br>0.01 | 100<br>0 |
| iso-C₃H₇O-P(=S)(CH₃)-O-C₆H₃(Br)-SO₂-CH₂-Cl (11) | 0.1<br>0.01 | 100<br>100 |
| C₂H₅O-P(=S)(C₂H₅)-O-C₆H₃(Br)-SO₂-CH₂-Cl (10) | 0.1<br>0.01 | 100<br>100 |

EXAMPLE 2

Phaedon larvae test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all beetle larvae had been killed, whereas 0% meant that none of the beetle larvae had been killed.

The active compounds, the concentrations of the active compounds, the evaluation times and the results can be seen from the following table:

Table 2

| (Phaedon larvae test) | | |
|---|---|---|
| Active compound | Active compound concentration in % | Degree of destruction in % after 3 days |
| n-C₃H₇S-P(=S)(OC₂H₅)-O-C₆H₃(Cl)-SO₂-CH₂-Cl (B) | 0.1<br>0.01<br>0.001 | 100<br>90<br>0 |
| CH₃O-P(=S)(C₂H₅)-O-C₆H₄-SO₂-CH₂-Cl (17) | 0.1<br>0.01<br>0.001 | 100<br>100<br>85 |
| CH₃O-P(=S)(C₂H₅)-O-C₆H₃(Cl)-SO₂-CH₂-Cl (2) | 0.1<br>0.01<br>0.001 | 100<br>100<br>100 |

Table 2-continued
(Phaedon larvae test)

| Active compound | Active compound concentration in % | Degree of destruction in % after 3 days |
|---|---|---|
| 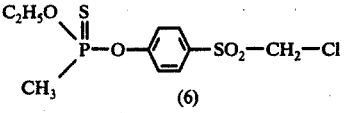 (6) | 0.1<br>0.01<br>0.001 | 100<br>100<br>100 |
| 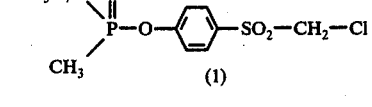 (1) | 0.1<br>0.01<br>0.001 | 100<br>100<br>95 |
| 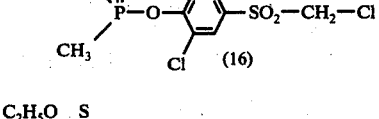 (16) | 0.1<br>0.01<br>0.001 | 100<br>100<br>95 |
| 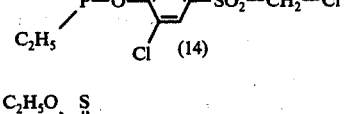 (14) | 0.1<br>0.01<br>0.001 | 100<br>100<br>100 |
| 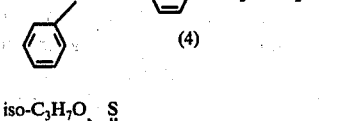 (4) | 0.1<br>0.01<br>0.001 | 100<br>100<br>90 |
| 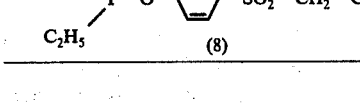 (8) | 0.1<br>0.01<br>0.001 | 100<br>100<br>100 |

EXAMPLE 3

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% meant that all the aphids were killed, whereas 0% meant that none of the aphids were killed.

The active compounds, the concentrations of the active compounds, the evaluation times and the results can be seen from the following table:

Table 3
(Myzus test)

| Active compound | Active compound concentration in % | Degree of destruction in % after 1 day |
|---|---|---|
| 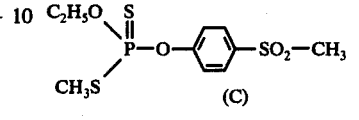 (C) | 0.1<br>0.01 | 35<br>0 |
| 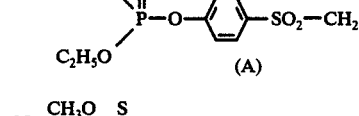 (A) | 0.1<br>0.01 | 90<br>0 |
| 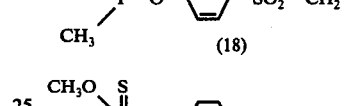 (18) | 0.1<br>0.01 | 100<br>100 |
| 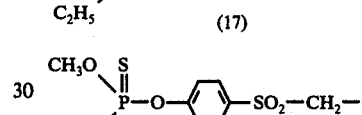 (17) | 0.1<br>0.01 | 100<br>99 |
| 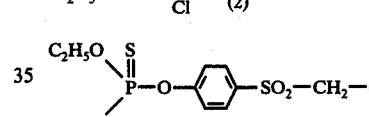 (2) | 0.1<br>0.01 | 100<br>98 |
| 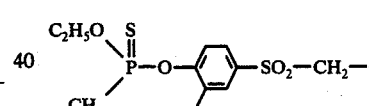 (6) | 0.1<br>0.01 | 100<br>100 |
| 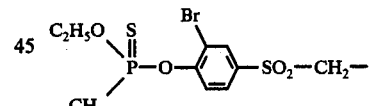 (15) | 0.1<br>0.01 | 100<br>100 |
| 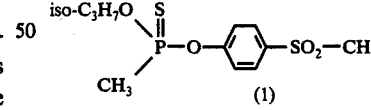 (12) | 0.1<br>0.01 | 100<br>100 |
| 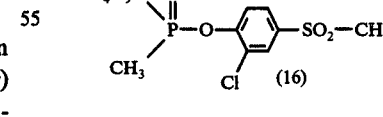 (1) | 0.1<br>0.01 | 100<br>100 |
| 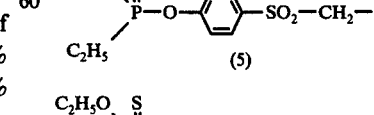 (16) | 0.1<br>0.01 | 100<br>95 |
| 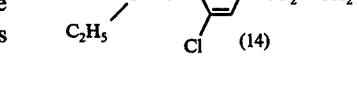 (5) | 0.1<br>0.01 | 100<br>100 |
|  (14) | 0.1<br>0.01 | 100<br>100 |

Table 3-continued
(Myzus test)

| Active compound | Active compound concentration in % | Degree of destruction in % after 1 day |
|---|---|---|
| n-C$_3$H$_7$O–P(=S)(C$_2$H$_5$)–O–C$_6$H$_4$–SO$_2$–CH$_2$–Cl  (9) | 0.1 / 0.01 | 100 / 100 |
| iso-C$_3$H$_7$O–P(=S)(C$_2$H$_5$)–O–C$_6$H$_4$–SO$_2$–CH$_2$–Cl  (8) | 0.1 / 0.01 | 100 / 100 |
| iso-C$_4$H$_9$O–P(=S)(C$_2$H$_5$)–O–C$_6$H$_4$–SO$_2$–CH$_2$–Cl  (7) | 0.1 / 0.01 | 99 / 95 |

EXAMPLE 4

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed, whereas 0% meant that none of the spider mites were killed.

The active compounds, the concentrations of the active compounds, the evaluation times and the results can be seen from the following table:

Table 4
(Tetranychus test)

| Active compound | Active compound concentration in % | Degree of destruction in % after 2 days |
|---|---|---|
| C$_2$H$_5$O–P(=S)(SCH$_3$)–O–C$_6$H$_4$–SO$_2$–CH$_3$  (C) | 0.1 / 0.01 | 30 / 0 |
| C$_2$H$_5$O–P(=S)(OC$_2$H$_5$)–O–C$_6$H$_4$–SO$_2$–CH$_2$–Cl  (D) | 0.1 / 0.01 | 50 / 0 |
| CH$_3$O–P(=S)(CH$_3$)–O–C$_6$H$_4$–SO$_2$–CH$_2$–Cl  (18) | 0.1 / 0.01 | 98 / 80 |

Table 4-continued
(Tetranychus test)

| Active compound | Active compound concentration in % | Degree of destruction in % after 2 days |
|---|---|---|
| C$_2$H$_5$O–P(=S)(CH$_3$)–O–C$_6$H$_4$–SO$_2$–CH$_2$–Cl  (6) | 0.1 / 0.01 | 100 / 100 |
| iso-C$_3$H$_7$O–P(=S)(CH$_3$)–O–C$_6$H$_4$–SO$_2$–CH$_2$–Cl  (1) | 0.1 / 0.01 | 99 / 95 |

EXAMPLE 5

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all the test insects had been killed and was 0% if exactly as many test insects were still alive as in the case of the untreated control.

The active compounds, amounts used and results can be seen from the table which follows:

Table 5
Soil insects
(*Tenebrio molitor* larvae in the soil)

| Active compound | Degree of destruction in % at an active compound concentration of 10 ppm |
|---|---|
| C$_2$H$_5$O–P(=S)(OC$_2$H$_5$)–O–C$_6$H$_4$–SO$_2$–CH$_2$–Cl  (D) | 0 |
| n-C$_3$H$_7$S–P(=S)(OC$_2$H$_5$)–O–C$_6$H$_4$–SO$_2$–CH$_2$–Cl  (A) | 0 |

Table 5-continued

Soil insects
*(Tenebrio molitor larvae in the soil)*

| Active compound | Degree of destruction in % at an active compound concentration of 10 ppm |
|---|---|
| (n-C$_3$H$_7$S)(C$_2$H$_5$O)P(=S)–O–(2-Cl-C$_6$H$_3$)–SO$_2$–CH$_2$–Cl  (B) | 0 |
| (C$_2$H$_5$O)(CH$_3$S)P(=S)–O–C$_6$H$_4$–SO$_2$–CH$_3$  (C) | 0 |
| (CH$_3$O)(C$_2$H$_5$)P(=S)–O–(2-Cl-C$_6$H$_3$)–SO$_2$–CH$_2$–Cl  (2) | 100 |
| (iso-C$_3$H$_7$O)(CH$_3$)P(=S)–O–C$_6$H$_4$–SO$_2$–CH$_2$–Cl  (1) | 100 |
| (C$_2$H$_5$O)(C$_6$H$_5$)P(=S)–O–C$_6$H$_4$–SO$_2$–CH$_2$–Cl  (4) | 100 |
| (C$_2$H$_5$O)(CH$_3$)P(=S)–O–C$_6$H$_4$–SO$_2$–CH$_2$–Cl  (6) | 100 |
| (iso-C$_4$H$_9$O)(C$_2$H$_5$)P(=S)–O–C$_6$H$_4$–SO$_2$–CH$_2$–Cl  (7) | 100 |
| (iso-C$_3$H$_7$O)(C$_2$H$_5$)P(=S)–O–C$_6$H$_4$–SO$_2$–CH$_2$–Cl  (8) | 100 |
| (n-C$_3$H$_7$O)(C$_2$H$_5$)P(=S)–O–C$_6$H$_4$–SO$_2$–CH$_2$–Cl  (9) | 100 |
| (C$_2$H$_5$O)(CH$_3$)P(=S)–O–(2-Br-C$_6$H$_3$)–SO$_2$–CH$_2$–Cl  (12) | 100 |

EXAMPLE 6

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all the test insects had been killed and was 0% if exactly as many test insects were still alive as in the case of the untreated control.

The active compounds, amounts used and results can be seen from the table which follows:

Table 6

Soil insects
*(Phorbia antiqua grubs in the soil)*

| Active compound | Degree of destruction in % at an active compound concentration of 10 ppm |
|---|---|
| (C$_2$H$_5$O)$_2$P(=S)–O–C$_6$H$_4$–SO$_2$–CH$_2$–Cl  (D) | 0 |
| (n-C$_3$H$_7$S)(C$_2$H$_5$O)P(=S)–O–C$_6$H$_4$–SO$_2$–CH$_2$–Cl  (A) | 0 |
| (n-C$_3$H$_7$S)(C$_2$H$_5$O)P(=S)–O–(2-Cl-C$_6$H$_3$)–SO$_2$–CH$_2$–Cl  (B) | 0 |
| (C$_2$H$_5$O)(CH$_3$S)P(=S)–O–C$_6$H$_4$–SO$_2$–CH$_3$  (C) | 0 |
| (iso-C$_3$H$_7$O)(CH$_3$)P(=S)–O–C$_6$H$_4$–SO$_2$–CH$_3$  (1) | 100 |
| (C$_2$H$_5$O)(C$_6$H$_5$)P(=S)–O–C$_6$H$_4$–SO$_2$–CH$_2$–Cl  (4) | 100 |
| (C$_2$H$_5$O)(C$_2$H$_5$)P(=S)–O–C$_6$H$_4$–SO$_2$–CH$_2$–Cl  (5) | 100 |
| (C$_2$H$_5$O)(CH$_3$)P(=S)–O–C$_6$H$_4$–SO$_2$–CH$_2$–Cl  (6) | |

Table 6-continued

Soil insects
(*Phorbia antiqua* grubs in the soil)

| Active compound | Degree of destruction in % at an active compound concentration of 10 ppm |
|---|---|
| iso-$C_4H_9O$\\$P$(=S)/$C_2H_5$ —O—⟨Ph⟩—$SO_2$—$CH_2$—Cl  (7) | 100 |
| iso-$C_3H_7O$\\$P$(=S)/$C_2H_5$ —O—⟨Ph⟩—$SO_2$—$CH_2$—Cl  (8) | 100 |
| n-$C_3H_7O$\\$P$(=S)/$C_2H_5$ —O—⟨Ph⟩—$SO_2$—$CH_2$—Cl  (9) | 100 |
| $C_2H_5O$\\$P$(=S)/$C_2H_5$ —O—⟨Ph, Br⟩—$SO_2$—$CH_2$—Cl  (10) | 100 |
| iso-$C_3H_7O$\\$P$(=S)/$CH_3$ —O—⟨Ph, Br⟩—$SO_2$—$CH_2$—Cl  (11) | 100 |
| $C_2H_5O$\\$P$(=S)/$CH_3$ —O—⟨Ph, Br⟩—$SO_2$—$CH_2$—Cl  (12) | 100 |
| iso-$C_4H_9O$\\$P$(=S)/$C_2H_5$ —O—⟨Ph, Br⟩—$SO_2$—$CH_2$—Cl  (13) | 100 |
| $C_2H_5O$\\$P$(=S)/$C_2H_5$ —O—⟨Ph, Cl⟩—$SO_2$—$CH_2$—Cl  (14) | 100 |
| $C_2H_5O$\\$P$(=S)/$CH_3$ —O—⟨Ph, Cl⟩—$SO_2$—$CH_2$—Cl  (15) | 100 |
| sec.-$C_4H_9O$\\$P$(=S)/$CH_3$ —O—⟨Ph, Cl⟩—$SO_2$—$CH_2$—Cl  (16) | 100 |

EXAMPLE 7

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (= mg/l), was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage: The degree of effectiveness was 100% when infestation had been completely avoided; it was 0% when the infestation was exactly the same as in the case of the control plants in untreated soil which had been infested in the same manner.

The active compound, the amounts applied and the results can be seen from the following table:

Table 7

Nematodes (*Meloidogyne incognita*)

| Active compound | Degree of destruction in % at an active compound concentration of 10 ppm |
|---|---|
| $C_2H_5O$\\$P$(=S)/$C_2H_5O$ —O—⟨Ph⟩—$SO_2$—$CH_2$—Cl  (D) | 0 |
| n-$C_3H_7S$\\$P$(=S)/$C_2H_5O$ —O—⟨Ph⟩—$SO_2$—$CH_2$—Cl  (A) | 0 |
| n-$C_3H_7S$\\$P$(=S)/$C_2H_5O$ —O—⟨Ph, Cl⟩—$SO_2$—$CH_2$—Cl  (B) | 0 |
| $C_2H_5O$\\$P$(=S)/$CH_3S$ —O—⟨Ph⟩—$SO_2$—$CH_3$  (C) | 0 |
| $C_2H_5O$\\$P$(=S)/$C_2H_5$ —O—⟨Ph⟩—$SO_2$—$CH_2$—Cl  (5) | 100 |
| n-$C_3H_7O$\\$P$(=S)/$C_2H_5$ —O—⟨Ph⟩—$SO_2$—$CH_2$—Cl  (9) | 100 |

EXAMPLE 8

Test with parasitic nematodes

Infectious larvae III of *Haemonchus contortus* were exposed, in vitro, to aqueous dilutions of the test substances and after 3 hours the mobility of the larvae was assessed microscopically in comparison to untreated controls.

The following figures of merit were used:
3 = all larvae extended and motionless
2 = larvae spirally coiled up, in part still slightly mobile
1 = movement of the larvae clearly slowed down in comparison to the controls, or rapid tremulous movement
0 = normally mobile, as in the controls.

The active compounds tested and the results obtained may be seen from the table which follows:

Table 8

Test with parasitic nemotodes

| Active compound | Concentration in μg/ml | Rating |
|---|---|---|
| $C_2H_5O$ \ S ‖ P—O—⟨⟩—$SO_2$—$CH_2$—Cl / $CH_3$ (6) | 10,000<br>1,000<br>100<br>30<br>10 | 3<br>3<br>3-2<br>2<br>1<br>0 |
| $C_2H_5O$ \ S ‖ P—O—⟨⟩—$SO_2$—$CH_2$—Cl / $C_2H_5$ (5) | 10,000<br>1,000<br>100<br>30<br>10 | 2<br>2<br>2<br>1<br>0 |

The process of the present invention is illustrated by the following preparative examples. The preparation of the starting materials (II), in which R″ represents hydrogen or chlorine, is described in U.S. patent application Ser. No. 648,849, now U.S. Pat. No. 4,013,794

Where R″ represents bromine, the compounds can, for example, be prepared as follows:

EXAMPLE 9

HO—⟨⟩—$SO_2$—$CH_2$Cl
     |
     Br 160 g (1 mole) of bromine were added dropwise at room temperature to a solution of 206.5 g (1 mole) of 4-chloromethylsulfonylphenol in 500 ml of glacial acetic acid; the mixture was stirred for a further hour at 45° C and, when it has cooled, was poured onto 1.5 l of ice-water. The product which had precipitated was filtered off and recrystallized from toluene. 185 g (65% of theory) of 2-bromo-4-chloromethylsulfonylphenol were thus obtained as a colorless powder of melting point 158°-160° C.

EXAMPLE 10 iso-$C_3H_7O$ \ S ‖ P—O—⟨⟩—$SO_2$—$CH_2$Cl / $CH_3$ (1)

A mixture of 20.7 g (0.1 mole) of 4-chloromethylsulfonylphenol, 15.2 g (0.11 mole) of potassium carbonate, 300 ml of acetonitrile and 17.3 g (0.1 mole) of O-isopropylmethanethionophosphonic acid ester chloride was stirred for 2 hours at 45° C. After adding 400 ml of toluene, the reaction mixture was washed twice with 300 ml of water each time, the organic phase was dried over sodium sulfate and the solvent was removed under reduced pressure. The residue was subjected to slight distillation. 24.3 g (72% of theory) of O-isopropyl-O-(4-chloromethylsulfonylphenyl)-methanethionophosphonic acid ester were thus obtained in the form of colorless crystals of melting point 59° C.

The following compounds of the formula $$\text{RO} \diagdown \overset{S}{\underset{\|}{P}}-O-\underset{R''}{\underset{|}{\langle\rangle}}-SO_2CH_2Cl \quad (I)$$
$$R' \diagup$$

could be prepared analogously:

Table 9

| Compound No. | R | R' | R″ | Yield (% of theory) | Refractive index: melting point, °C |
|---|---|---|---|---|---|
| 2 | $CH_3$— | $C_2H_5$— | Cl | 55 | $n_D^{21}$: 1.5735 |
| 3 | $C_2H_5$— | ⟨⟩— | Cl | 64 | $n_D^{21}$: 1.5961 |
| 4 | $C_2H_5$— | ⟨⟩— | H | 66 | $n_D^{24}$: 1.5909 |
| 5 | $C_2H_5$— | $C_2H_5$— | H | 75 | $n_D^{24}$: 1.5575 |
| 6 | $C_2H_5$— | $CH_3$— | H | 68 | $n_D^{20}$: 1.5642 |
| 7 | iso-$C_4H_9$— | $C_2H_5$— | H | 52 | $n_D^{20}$: 1.5456 |
| 8 | iso-$C_3H_7$— | $C_2H_5$— | H | 51 | $n_D^{20}$: 1.5531 |
| 9 | n-$C_3H_7$— | $C_2H_5$— | H | 44 | $n_D^{20}$: 1.5488 |
| 10 | 5—$2H_5$— | $C_2H_5$— | Br | 70 | $n_D^{26}$: 1.5832 |
| 11 | iso-$C_3H_7$— | $CH_3$— | Br | 38 | 110 |
| 12 | $C_2H_5$— | $CH_3$— | Br | 52 | $n_D^{26}$: 1.5900 |
| 13 | iso-$C_4H_9$— | $C_2H_5$— | Br | 64 | $n_D^{23}$: 1.5681 |
| 14 | $C_2H_5$— | $C_2H_5$— | Cl | 94 | $n_D^{24}$: 1.5550 |
| 15 | $C_2H_5$— | $CH_3$— | Cl | 85 | $n_D^{24}$: 1.5672 |
| 16 | sec.-$C_4H_9$— | $CH_3$— | Cl | 84 | $n_D^{24}$: 1.5528 |
| 17 | $CH_3$— | $C_2H_5$— | H | 64 | $n_D^{29}$: 1.5675 |
| 18 | $CH_3$— | $CH_3$— | H | 41 | $n_D^{20}$: 1.5808 |

It will be appreciated that the instant specification and examples are set forth by way of illustration and not limitation, and that various modifications and changes may be made without departing from the spirit and scope of the present invention.

What is claimed is:

1. An O-alkyl-O-(4-chloromethylsulfonylphenyl)thionophosphonic acid ester of the formula $$\text{RO} \diagdown \overset{S}{\underset{\|}{P}}-O-\underset{R''}{\underset{|}{\langle\rangle}}-SO_2-CH_2-Cl$$
$$R' \diagup$$

in which
R represents alkyl with 1 to 6 carbon atoms,
R' represents alkyl with 1 to 6 carbon atoms or phenyl, and
R″ represents hydrogen or halogen.

2. An ester according to claim 1, in which R represents straight-chain or branched alkyl with 1 to 4 carbon atoms, R' represents straight-chain or branched alkyl with 1 to 3 carbon atoms or phenyl, and R″ represents hydrogen, chlorine or bromine.

3. The compound according to claim 1 wherein such compound is O-isopropyl-O-(4-chloromethylsulfonylphenyl)-methanethionophosphonic acid ester of the formula

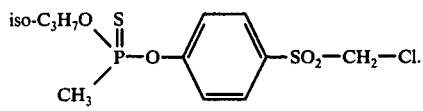

4. The compound according to claim 1 wherein such compound is O-isobutyl-O-(4-chloromethylsulfonylphenyl)-ethane thionophosphonic acid ester of the formula

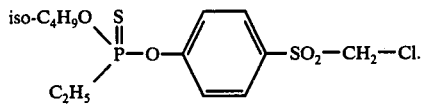

5. The compound according to claim 1 wherein such compound is O-isopropyl-O-(4-chloromethylsulfonylphenyl)-ethanethionophosphonic acid ester of the formula

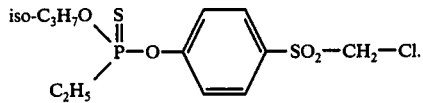

6. The compound according to claim 1 wherein such compound is O-n-propyl-O-(4-chloromethylsulfonylphenyl)-ethanethionophosphonic acid ester of the formula

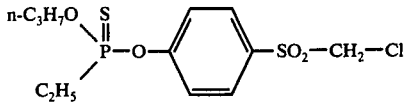

7. The compound according to claim 1 wherein such compound is O-ethyl-O-(2-chloro-4-chloromethylsulfonyl-phenyl)methanethionophosphonic acid ester of the formula

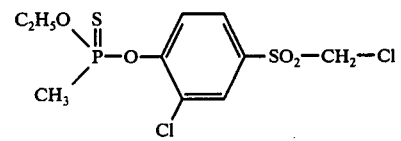

8. A nematicidal or arthropodicidal composition containing as active ingredient a nematicidally or arthropodicidally effective amount of an ester according to claim 1 in admixture with a diluent.

9. A method of combating nematodes or arthropods which comprises applying to the nematodes or arthropods, or to a habitat thereof, a nematicidally or arthropodicidally effective amount of an ester according to claim 1.

10. The method according to claim 9, in which said ester is
O-isopropyl-O-(4-chloromethylsulfonylphenyl)-methanethionophosphonic acid ester,
O-isobutyl-O-(4-chloromethylsulfonylphenyl)-ethanethionophosphonic acid ester,
O-isopropyl-O-(4-chloromethylsulfonylphenyl)-ethanethionophosphonic acid ester,
O-n-propyl-O-(4-chloromethylsulfonylphenyl)-ethanethionophosphonic acid ester, or
O-ethyl-O-(2-chloro-4-chloromethylsulfonyl-phenyl)-methanethionophosphonic acid ester.

* * * * *